United States Patent [19]

Horiguchi et al.

[11] Patent Number: 4,897,370
[45] Date of Patent: Jan. 30, 1990

[54] PROCESS FOR PREPARING CERAMICS COMPOSITE SINTERED BODIES

[75] Inventors: Yasunobu Horiguchi, Kamagaya; Nobuyuki Yamamoto, Edogawa; Tuyoshi Goto, Kawasaki, all of Japan

[73] Assignee: Lion Corporation, Tokyo, Japan

[21] Appl. No.: 213,307

[22] Filed: Jun. 29, 1988

[30] Foreign Application Priority Data

Jun. 30, 1987 [JP] Japan .................................. 62-162707
Jun. 30, 1987 [JP] Japan .................................. 62-162708
Jun. 30, 1987 [JP] Japan .................................. 62-162709

[51] Int. Cl.$^4$ ...................... C03C 10/00; C03C 14/00
[52] U.S. Cl. .......................................... 501/5; 501/10; 501/12; 501/32; 501/63; 501/72; 501/73; 501/95
[58] Field of Search .................... 501/12, 5, 10, 63, 95, 501/32, 72, 73

[56] References Cited

U.S. PATENT DOCUMENTS

| | | | |
|---|---|---|---|
| 3,767,434 | 10/1973 | Thomas .................................. | 501/12 |
| 3,847,583 | 11/1974 | Dislich et al. ..................... | 501/63 X |
| 4,230,455 | 10/1980 | Hidaka et al. ......................... | 433/202 |
| 4,485,179 | 11/1984 | Brennan et al. ................... | 501/95 X |
| 4,560,666 | 12/1985 | Yoshida et al. ..................... | 501/73 X |
| 4,588,699 | 5/1986 | Brennan et al. ................... | 501/95 X |
| 4,589,900 | 5/1986 | Brennan et al. ................... | 501/95 X |
| 4,755,489 | 7/1988 | Chyung et al. ..................... | 501/95 X |
| 4,766,096 | 8/1988 | Layden et al. ..................... | 501/95 X |

FOREIGN PATENT DOCUMENTS

| | | |
|---|---|---|
| 0104640 | 4/1984 | European Pat. Off. . |
| 0145210 | 6/1985 | European Pat. Off. . |
| 2725665 | 12/1977 | Fed. Rep. of Germany . |
| 60-246254 | 12/1985 | Japan . |
| 61-234867 | 10/1986 | Japan . |
| 2187142 | 8/1987 | Japan . |

*Primary Examiner*—Mark L. Bell
*Assistant Examiner*—Karl Group
*Attorney, Agent, or Firm*—Burns, Doane, Swecker and Mathis

[57] ABSTRACT

A process for preparing a glass or glass-ceramic composite sintered body by a sol-gel method comprises reacting
(A) at least one silicic acid ester represented by the general formula (I).

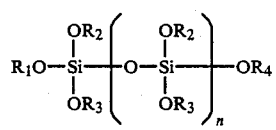

wherein $R_1$ to $R_4$ are each hydrogen or a group represented by Chd $xH_{2x+1}(OC_2H_4)_y$— wherein x is 1 to 5, and y is 0 to 10, provided that $R_1$ to $R_4$ are not all hydrogen at the same time, and n is 0 to 20;
(B) at least one phosphorus compound represented by the general formula (II), (III) or (IV):

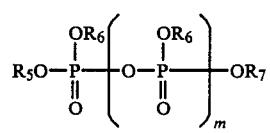

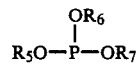

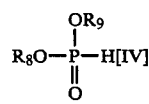

wherein $R_5$ to $R_9$ are each hydrogen, an alkyl group having 1 to 5 carbon atoms, a phenyl group or an aralkyl group having 7 to 10 carbon atoms, and m is 0 to 10; and
(C) at least one compound selected from the group consisiting of calcium salts and calcium coumpounds represented by the general formula (V)

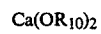

wherein $R_{10}$ represents an alkyl group having 1 to 5 carbon atoms; with water in the presence of the follwing componentn (D-1) and/or the following component (D-2) to form a gel, and drying, molding and then sintering the gel;
(D-1): at least one kind of ceramics fine particles having a composition different from a sintered body obtained form components (A) to (C) or having a crystal different from crystals formed in the sintered body,
(D-2): ceramic short fibers and/or whiskers.

$SiO_2$-$P_2O_5$-CaO glass or glass-ceramic composite sintered body contains at least one of ceramics short fibers and/or whiskers, and at least one of ceramics fine particles.

According to the invention, there can be obtained composite sintered bodies of calcium phosphate glasses or glass-ceramics exhibiting excellent in biocompatibility in which ceramics fine particles, ceramics fibers and whiskers are uniformly dispersed and mixed, and strength, toughness and scatter of strength are effectively improved.

Thus the composite sintered bodies of the invention are widely applicable as materials for hard tissue of living bodies such as artificial tooth roots and artificial bones.

13 Claims, No Drawings

PROCESS FOR PREPARING CERAMICS COMPOSITE SINTERED BODIES

BACKGROUND OF THE INVENTION (1) Field of the Invention

The invention relates to a process for preparing glass or glass-ceramic composite sintered bodies excellent biocompatibility, particularly such sintered bodies useful as artificial bones or tooth roots. The invention also relates to novel ceramics composite sintered bodies excellent in biocompatibility.

(2) Prior Art

Various ceramics materials have been proposed together with apatites as materials for hard tissues of living bodies such as artificial bones or artificial tooth roots. Among them, calcium phosphate glasses or glass-ceramics have drawn particularly attention as materials directly binding to bones, and have been prepared according to the melting method, the sol-gel method and other such methods.

On the other hand, ceramics materials which have hitherto been proposed as materials directly binding to bones are generally inadequate in strength. As a result, members consisting of ordinary ceramic materials have to be made thick at the part in living bodies where the load is high, and the range of applicability thereof have been limited.

Under the circumstances, for solution of such problems it has been proposed to incorporate various ceramics fine particles, short fibers, whiskers, etc. in the ceramics matrices of the aforesaid ceramics members as reinforcing materials. For example, use of fibers or whiskers of metals, ceramics or glass as a core material (Japanese Patent Publication for Opposition Purpose (hereinafter referred to as "J.P. KOKOKU") No. 59-219), use of carbon fibers and mineral fibers (in Japanese Patent Unexamined Published Application (hereinafter referred to as "J.P. KOKAI") Nos. 59-57970 and 59-57971), and use of ceramics short fibers or whiskers (J.P. KOKAI No. 61-234867) have been proposed. However, all of the ceramics disclosed in the above publications are prepared by mixing a matrix component with a reinforcing material in a dry or wet state and sintering the mixture, and a process for preparation of ceramics by the sol-gel method is not disclosed therein.

On the other hand, glass has hitherto been prepared according to a melting method or VAD (Vaper-Phase Axial Deposition method), and glass-ceramics have been obtained by subjecting glass to a crystallizing treatment. However, sol-gel methods have the advantages that glass-ceramics can be synthesized at a low temperature, glass-ceramics having high purity can be obtained, and no limitation due to range of vitrification arises, which is different from the case in a melting method, and thus sol-gel methods have attracted attention. As for sol-gel method, J.P. 60-246254 discloses a process by a sol-gel method of preparing ceramics wherein whiskers etc. are dispersed in the ceramics matrix, by mixing a dispersion of ceramic particles and/or whiskers in water with a metal alkoxide. However, the metal alkoxides used therein are those for machinery members such as aluminum alkoxides, and there is no disclosure therein about preparation of calcium phosphate ceramics useful for living body materials.

Thus, there has been desired a process for effectively preparing reinforced calcium phosphate ceramics, which have recently drawn particular attention, by a sol-gel method.

SUMMARY OF THE INVENTION

The primary object of the invention is to provide an excellent process for preparing composite sintered bodies wherein calcium phosphate glasses or glass-ceramics, as a matrix having high biocompatibility, is reinforced with (D-1) ceramics fine particles and/or (D-2) ceramic short fibers and/or whiskers.

Another object of the invention is to provide novel ceramic composite sintered bodies containing ceramic fine particles, ceramics short fibers and/or whiskers as reinforcing materials.

The invention has been accomplished based on the finding that when gel is formed by reacting a certain silicic acid ester, a certain phosphorus compound and a certain calcium compound with water, the above object can effectively be attained by carrying out the gelation reaction in the presence of ceramics fine particles, ceramic short fibers or whiskers.

More specifically, the invention provides a process for preparing a glass or glass-ceramic composite sintered body which comprises reacting (A) at least one silicic acid ester represented by the general formula (I):

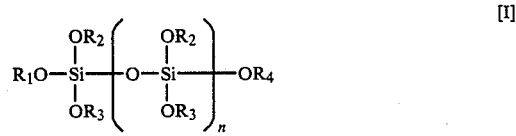

wherein $R^1$ to $R_4$ are each hydrogen or a group represented by $C_xH_{2x+1}(OC_2H_4)_y-$ wherein x is 1 to 5, and y is 0 to 10, provided that $R^1$ to $R_4$ are not all hydrogen at the same time, and n is 0 to 20;

(B) at least one phosphorus compound represented by the general formula (II), (III) or (IV):

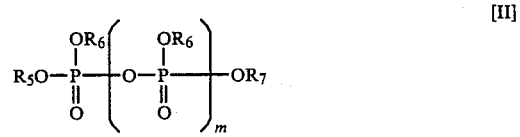

wherein $R_5$ to $R_9$ are each hydrogen, an alkyl group having 1 to 5 carbon atoms, a phenyl group or an aralkyl group having 7 to 10 carbon atoms, and m is 0 to 10; and (C) at least one compound selected from the group consisting of calcium salts and calcium compounds represented by the general formula (V)

$$Ca(OR_{10})_2 \qquad (V)$$

wherein $R_{10}$ represents an alkyl group having 1 to 5 carbon atoms; with water in the presence of the following component (D-1) and/or the following component (D-2) to form a gel, and drying, molding and then sintering the gel;

(D-1): at least one kind of ceramics fine particles having a composition different from a sintered body obtained from components (A) to (C) or having a crystal different from crystals formed in the sintered body, (D-2): ceramic short fibers and/or whiskers.

The invention also provides a novel $SiO_2$—$P_2O_5$—$CaO$ glass or glass-ceramic composite sintered body containing component (D-1) and component (D-2).

Preferred Embodiments of the Invention

As silicic acid esters represented by the general formula (I) as used in the invention, those wherein $R^1$ to $R_4$ are $CH_3$, $C_2H_5$, $n$-$C_3H_7$, iso-$C_3H_7$, $n$-$C_4H_9$ or —$C_2H_4OCH_3$ in the formula (I) are preferable, and among these those wherein $R^1$ to $R_4$ are the same group are particularly preferred. In the invention, those wherein n is 0 are preferable, and those wherein n is 1 to 10 are also preferable. Specific examples of silicic acid esters represented by the general formula (I) include tetramethoxysilane, tetraethoxysilane, tetra(n-propoxy)silane, tetraisopropoxysilane, tetrabutoxysilane, tetra(2-methoxyethoxy)silane, and oligomers (2 to 10 monomers) of these silicates. Of these examples, tetraethoxysilane $Si(OC_2H_5)_4$ can be readily obtained as Ethyl Silicate 28 from Colcoat Co., Ltd. and a 5-mol-average condensation product of tetraethoxysilane:

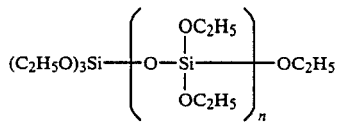

n = 4 can also be obtained as Ethyl Silicate 40 from Colcoat Co., Ltd. The above silicic acid esters can be used alone or in combinations of two or more of them.

The concentration of silicic acid esters in the reaction mixture can be optionally changed, but is preferably 0.1 to 40 weight % (hereinafter abbreviated as %), particularly preferably 2 to 30% in terms of $SiO_2$ amount in the reaction mixture of matrix components except components (D-1) and (D-2).

As the phosphorus compound in the invention there can be used one compound represented by the general formulae (II), (III) and (IV) or a mixture of two or more of them.

As phosphoric acid esters of the formula (II), those wherein $R_5$ to $R_7$ are alkyl groups having 1 to 4 carbon atoms in the formula (II) are preferable, and those wherein $R_5$ to $R_7$ are phenyl groups or benzyl groups are also prefered. Further, m is preferably 0 to 4. Further, phosphoric acid esters wherein all of $R_5$ to $R_7$ are alkyl groups, phosphoric acid wherein all of $R_5$ to $R_7$ are hydrogen and condensates thereof, and partial esters containing both alkyl group(s) and hydrogen can all be used. Further, in phosphorous acid and phosphorous acid esters represented by the general formulae (III) and (IV), as the alkyl group those having 1 to 4 carbon atoms are preferable, and a phenyl group and a benzyl group are also preferable. Specific examples of preferred compounds include those wherein $R_5$ to $R_9$ are methyl, ethyl, iso-propyl, n-propyl, n-butyl, phenyl and benzyl in the general formulae (III) and (IV).

Among the above various phosphorus compounds in the invention, most preferable are those of the formula (II) wherein at least one of $R_5$ to $R_7$ is hydrogen, but all of them are not hydrogen at the same time. As specific examples the following compounds alone and mixtures of two or more of them can be mentioned.

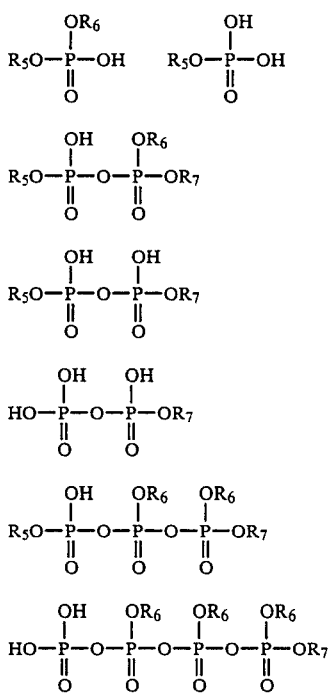

$R_5$ to $R_7$ in the above formulae are the same as $R_5$ to $R_7$ in the formula (II) except that hydrogen is excluded.

The above partial esters of phosphoric acid can be readily obtained, for example, by partially hydrolizing the corresponding phosphoric acid esters, by adding phosphoric acids to the corresponding alcohols to carry out esterification, or by reacting phosphorus pentaoxide with alcohols and hydrolizing the product.

Calcium ion can be mentioned as another essential component of the invention, and calcium salts or compounds represented by the above general formula (V) are used as substances forming the ion. These substances are used since addition of Ca is necessary for preparing bio-active glasses or glass-ceramics. Calcium salts include, for example, calcium nitrate, calcium acetate, calcium chloride, calcium hydroxide, calcium hydrogen citrate, calcium citrate and calcium oxalate. Among these calcium components, water soluble salts such as calcium nitrate, calcium acetate and calcium chloride are particularly preferred.

Further, in the invention there can be added besides the above constitutive elements, elements which can become constitutive oxides of gel, namely glass or glass-ceramics which are the matrix of the sintered body. These elements are specifically Li, Na, K, Mg, Al, Zr, Ti, B, etc., and these elements can be used either in the form of metal alkoxides or in the form of soluble salts. These compounds are suitably used in an amount of a 0 to 30% in terms of oxide based on the total amount of the oxides when all of gel constituting elements are converted to oxides.

In the invention, the matrix of composite sintered body is formed using the above components. Therefore, it is desirable to use components (A) to (C) so that the rate of the respective components in $SiO_2$—$P_2O_5$—$CaO$, which is the fundamental component of the matrix, falls within the following range.

$SiO_2$: 20 to 70%, preferably 30 to 60%.

Below 20% the strength of the sintered body is not adequately exhibited, and above 70% the relative content of $P_2O_5$ and CaO becomes smaller, and as a result the binding power with bones is weaken.

$P_2O_5$: 1 to 40%, preferably 2 to 30%.

Below 1% the biding power with bones is weaken, and above 40% chemical durability is lowered and the matrix is liable to dissolve in humor.

CaO: 10 to 60%, preferably 20 to 55%.

Below 10% or above 60% the strength and chemical durability are lowered.

Further, in the invention it is desirable that the total content of $SiO_2$, CaO and $P_2O_5$ which are the above 3 components is 70% or more, preferably 80% or more.

The invention is characterized in that when the above components are reacted with water to form a gel, the gelation reaction is carried out in the presence of components (D-1) and/or (D-2).

Component (D-1)

Component (D-1) used herein plays a role in enhancement of strength of the matrix, and it is necessary to use as component (D-1) polycrystals or single crystals having a crystal different from those of crystal components formed in the matrix and having a melting point above the sintering temperature in preparation of the composite sintered bodies of the invention. These polycrystals or single crystals are ceramics known as oxides, carbides, nitrides, oxynitrides, borides, etc. of metal, and specifically include fine particles of $Al_2O_3$, $ZrO_2$, SiC, $Si_3N_4$, BN, sialon, etc. These fine particles can be used alone or in combination. Further, these fine particles can also be used in the form of fine particles of composite ceramics obtained by previously mixing and sintering them.

The reason why crystals different from the crystal components formed in the matrix are used is that when the same crystal is used, not much effect of strength enhancement can be expected.

Further, it is suitable that the particle size of the ceramics fine particles be 10 μm or less, preferably 5 μm or less. When the particle size is larger than 10 μm, the effect of strength enhancement is low. Further, it is suitable to use ceramics fine particles having an aspect ratio of below 5.

The ceramics fine particles may come to fall within the above range for their particle sizes by pulverizing the fine particles in a composite state with the matrix gel in the later-mentioned preparation steps of the composite sintered body of the invention. However, it is preferable to use ceramics fine particles having the above size from the beginning. This is because when ceramics fine particles are made smaller by pulverization, the matrix gel and the ceramics fine particles are mixed in a powdery state, and thus uniformity of the product is lowered as compared with mixing before gelation, namely mixing in a solid-liquid system, which is a characteristic of the invention.

Component (D-2)

Ceramics short fibers and whiskers used herein play a role in strength enhancement of the matrix, and include those using as raw materials oxides, carbides, nitrides, oxynitrides, borides, etc. of metal, all ordinary ceramics. There can be specifically mentioned short fibers and whiskers of $Al_2O_3$, $ZrO_2$, SiC, $Si_3N_4$, BN, sialon, etc.

Any kind of ceramic short fiber or whisker can be used so long as it has a melting point above the sintering temperature in the sintering step in preparation of composite sintered body of the invention. However, it is preferred to use those that are crystalline and have a crystal which is not transformed by heating in the sintering step. This is because when crystallization or crystal transformation takes place in the sintering step, the effect of strength enhancement essentially desired is decreased, for example, occuring to change of the thermal expansion coefficient, and the binding power of the interface with the matrix is lowered.

As ceramics short fibers and whiskers having the above characteristics, there can be mentioned α-$Al_2O_3$ as $Al_2O_3$; as $ZrO_2$ stabilized $ZrO_2$ and partially stabilized $ZrO_2$, CaO, MgO, $Y_2O_3$, etc. doped by; α-SiC and β-SiC as SiC, etc. As these short fibers and whiskers, those having an aspect ratio of 5 or more, preferably 10 or more and having a length of 2 μm to 5 mm are suitably used.

Component (D-1) can be used in an optional amount in the invention, but is suitably used in an amount of 5 to 60 volume %, preferably 10 to 55 volume % in the composite sintered body. Below 5 volume % the effect is low, and above 60 volume % the binding power with bones is weakened.

Component (D-2) can also be used in an optional amount, but is suitably used in an amount of 5 to 50 volume %, preferably 10 to 40 volume % in the composite sintered body. Below 5 volume %, the resulting effect is low, and above 50 volume % opposite effects take place. For example, the sintered density is not enhanced or the binding power with bones is lowered.

When components (D-1) and (D-2) are used together, it is suitable to use them so that the total amount of components is 10 to 60 volume %, preferably 15 to 55 volume %.

In the invention, components (D-1) and/or (D-2) are added thereto before gelation of components (A) to (C) forming the fundamental skeleton of the composite sintered bodies, and the mixture is made to gel, dried, molded and sintered to prepare a desired product. Conditions and the like of the respective preparation steps are shown below.

pH Condition at the gelation reaction

It is necessary to carry out the process of the invention in an acidic or neutral condition wherein the phosphorus component and the calcium component are mutually dissolved to form a uniform gel, preferably at a pH of 4 or less.

To acidify the solution, it is suitable to use a mineral acid such as hydrochloric acid, nitric acid, sulfuric acid or hydrofluoric acid, or an organic acid such as acetic acid, citric acid or lactic acid.

However, when phosphoric acid, phosphorous acid or partial ester of these acids is used as a phosphorus component in the invention, there is no need to newly add a pH adjusting agent because the phosphorous component is an acid. Further, when phosphoric acid esters or phosphorous acid esters are used, it is preferable to add the above acidic substances. The pH of the solution may be either constant until gelation or increased after the silicic acid ester has been partially hydrolyzed in order to promote gelation. Increase of the pH can be carried out by addition of an alkali such as aqueous ammonia, an amine or formamide.

Reaction solvent

Solvents for dissolving the above silicic acid esters, phosphorus components and calcium components include water, and alcohols such as methanol and ethanol, and mixtures thereof. Water is indispensable for forming gel by reaction with components (A) to (C). The amount of water to be used is that necessary for hydrolyzing these compounds, and is generally 1 equivalent weight or more, preferably 1 to 15 equivalent weight based on these compounds.

Specific process for preparation of gel

Gel is prepared using the above components, for example, according to any of the following processes in the invention.

(i) Phosphorus compound is added to silicic acid ester to partially hydrolyze the silicic acid ester, and calcium compound is then added thereto to complete gelation;

(ii) Silicic acid ester is partially hydrolyzed, phosphorus compound is added, and calcium compound is then added thereto to complete gelation;

(iii) Calcium compound is added to silicic acid ester to partially hydrolyze the silicic acid ester, and phosphorus compound is then added thereto to complete gelation;

(iv) Silicic acid ester is partially hydrolyzed, calcium compound is added, and phosphorus compound is added thereto to complete gelation;

(v) Silicic acid ester is added to a solution of phosphorus compound and calcium compound to form gel;

(vi) Silicic acid ester, phosphorus compound and calcium compound are mixed at the same time to form gel.

Gelation by the above hydrolyzation and polycondensation can be carried out either at room temperature or with heating. When the gelation is carried out at a temperature higher than the boiling point of the solvent used, it may be carried out under pressure with use of an autoclave, etc.

Process of addition of component (D-1) and/or (D-2)

Addition of component (D-1) and/or (D-2) may be carried out any time before gelation of the above components, and can for example be carried out by any of the following processes.

(i) Component (D-1) and/or (D-2) is added in advance t one of silicic acid ester, phosphorus compound and calcium compound as raw materials;

(ii) It is added after partial hydrolyzation of silicic acid ester;

(iii) It is added after all the raw materials are mixed.

Further, component (D-1) and/or (D-2) may be either added as such to the above solution before gelation and mixed therewith and dispersed therein, or dispersed in water or a solvent used for the reaction and then added to the solution.

It is better to use a means such as stirring or ultrasonic wave agitation for uniformly dispersing these components in the reaction system. It is also suitable to use known surfactants or polymer dispersing agents.

Gelation after the above addition can be carried out according to the above process, but it is preferable to continue dispersion by stirring, ultrasonic wave agitation or the like until gelation is completed in order to maintain uniform dispersion in the gel.

Preparation of sintered bodies

There is generally used in silica glass, etc. as a method of preparing glass by the sol-gel method, a method wherein gel is dried under control of evaporation rate to prepare dried gel, which is sintered as it is. However, it is difficult to prepare the multicomponent gel of the invention without forming cracks in the dried gel, and moreover mixing with stirring, ultrasonic wave agitation or the like is carried out in order to maintain the dispersibility of component(s) (D-1) and/or (D-2), so that it is difficult to obtain a gel having an arranged shape. Therefore, in order to obtain sintered bodies, it is preferable to use a method in which dried gel containing component (D-1) and/or (D-2) is either powdered and then heat-treated, or heat-treated and then powdered; molded; and sintered.

Drying

Drying is carried out at 0° to 200° C. under atmospheric or reduced pressure. Wet gel may be either pulverized and then dried, or dried and then pulverized.

Heat treatment

In order to remove the remaining alkoxy groups on Si, P and Ca atoms, to further proceed with condensation polymerization of the gel and to almost complete the reaction among the constituting components, heat treatment is carried out at a temperature lower than the sintering temperature and equal to or higher than 200° C., preferably higher than 400° C. Heat treatment at below 200° C. does not bring about an adequate effect.

Molding and sintering

Molding and sintering can be carried out according to any of the following (i) to (iv) methods:

(i) The heat-treated powder is molded by a uniaxial press or a cold isostatic press (CIP), and then sintered at 800 to 1300° C. under atmospheric pressure;

(ii) The heat-treated powder is molded by a uniaxial press or a CIP, and then sintered by a gas pressure sintering furnace at 800° to 1300° C. at a pressure from higher than atmospheric pressure to not higher than about 100 atmospheres;

(iii) The heat-treated powder is sintered by a hot press at 800° to 1300° C.;

(iv) The molded heat-treated powder is directly sintered by a hot isostatic press (HIP), or sintered under atmospheric pressure and then further treated with a HIP.

When component (D-1) and/or (D-2) is oxide, it is proper to sinter it in air, whereas when component (D-1) and/or (D-2) is non-oxide, it is necessary to sinter it in an inert gas such as Ar or under vacuum.

It is suitable in the invention to add a halide for preventing the tendency of apatite crystals to decompose to tricalcium phosphate (TCP) and further prevent decomposition of apatite when the sintering temperature is raised for the purpose of making the sintered density higher. Specifically, by adding a halide in the preparation of the raw material powder before sintering, decomposition of hydroxyapatite is inhibited and a sintered body having apatite crystals is obtained more easily. Halides are particularly preferably chlorides or fluorides, and specifically include hydrochloric acid, calcium chloride, hydrofluoric acid, hydrosilicofluoric acid, calcium fluoride, etc.

As for the method of addition of the halide, it may be added in the solution before gelation; or the gel may be impregnated with a halide solution and then dried; or the dried powder or heat-treated powder may be re-treated with a halide solution. Amount of a halide to be added is preferably on the order of 0.003 to 3% as that of halogen ions based on the total amount of the matrix in terms of oxide.

Composite sintered body prepared by the process of the invention

The above gel components by the process of the invention are heat-treated and sintered to become calcium phosphate glasses or glass-ceramics. The matrix may be either glass or glass-ceramics, but is preferably glass-ceramics having crystals. This is because the strength thereof becomes higher due to the contained crystals, as compared glass.

The composite sintered bodies of the invention have a $SiO_2$—$P_2O_5$—CaO matrix, and fundamental crystals forming these matrices include the following ones:

Calcium phosphate crystal
hydroxyapatite, oxyapatite, fluorapatite, chlorapatite, tricalcium phosphate, tetracalcium phosphate, calcium pyrophosphate, calcium metaphosphate, etc.

Calcium silicate crystal
wollastonite ($CaO.SiO_2$), $3CaO.2SiO_2$, $3CaO.SiO_2$, $2CaO.SiO_2$, etc.

Calcium silicophosphate crystal
$7CaO.P_2O_5.2SiO_2$, $Ca_5(PO_4)_2SiO_4$, etc.

Crystals formed by other constitutive components to be added include the following crystals:

Magnesium silicate crystal
forsterite ($2MgO.SiO_2$), steatite ($MgO.SiO_2$), etc.

Calcium magnesium silicate crystal
diopside ($MgO.CaO.2SiO_2$), akermanite ($MgO.2CaO.2SiO_2$), etc.

Calcium sodium silicate crystal
$Na_2O.2CaO.3SiO_2$, $Na_2O.3CaO.2SiO_2$, $Na_2O.CaO.SiO_2$, etc.

Magnesium potassium silicate crystal
$K_2O.MgO.SiO_2$

Further, there can be mentioned crystals consisting of constitutive components such as sodium silicate, potassium silicate, sodium phosphate, potassium phosphate and silica alone or in various combination.

Among the above crystals, those comprising apatite are preferable, and those comprising apatite and wollastonite are particularly preferable.

According to the invention, there can be obtained composite sintered bodies of calcium phosphate glasses or glass-ceramics where ceramics fine particles and/or ceramics short fibers and/or whiskers are uniformly dispersed and mixed, and calcium phosphate glasses or glass-ceramics excellent in biocompatibility can be obtained with effectively improved strength, toughness and reduced scatter of the strength.

Thus composite sintered bodies of the invention are widely applicable as materials for hard tissue of living bodies such as artificial tooth root and artificial bone.

The invention is described below by examples, but is not limited thereto.

EXAMPLE 1

65.8 g of tetramethoxysilane (26.0 g in terms of $SiO_2$), 18.9 g of 85% orthophosphoric acid (11.6 g in terms of $P_2O_5$) and 90 g of water were mixed, and stirred at room temperature for one hour. Thereafter, 160 g of 50% aqueous solution of calcium nitrate (27.3 g in terms of CaO) was added, and 51.0 g (corresponding to 40 volume %) of β-SiC powder (average particle size: 1 μm) was added little by little while stirring was continued. Stirring of the mixture was continued for two more hours, and the temperature was then raised to 70° C. while stirring was continued, whereby the mixture thickened and gelled about 15 minutes thereafter. After cooling to room temperature, the gel was taken out and dried at 50° C. for one week. The gel was then pulverized, and the resulting powder was heat-treated by elevating the temperature to 500° C. at 20° C./hr and holding the powder at the temperature for 5 hours.

The resulting heat-treated powder was pulverized by a ball mill and then sintered by a hot press in an argon atmosphere under a pressure of 300 kg/cm² at 1150° C. for 2 hours.

The resulting sintered body contained crystals of apatite and wollastonite besides the mixed silicon carbide.

The evaluation of dynamic properties of the sintered bodies revealed remarkable enhancement of the properties in the sintered body obtained by the present example. Namely, the bending strength of the sintered body not containing the β-SiC powder (comparative example) was 2200 kg/cm², but that of the sintered body obtained by the present example was 5100 kg/cm², the fracture toughness of the former was 1.8 MPa·m½, but that of the latter was 3.1 MPa·m½.

EXAMPLE 2

114.8 g of tetraethoxysilane (33.2 g in terms of $SiO_2$), 9.9 g (5.1 g in terms of $P_2O_5$) of the mixture of monoethyl phosphate and diethyl phosphate (molar ratio: 50/50) and 100 g of water were mixed, and stirred at 40° C. for one hour. Thereafter, 110.6 g of 50% aqueous solution of calcium nitrate (18.9 g in terms of CaO) and 37.1 g of 30% aqueous solution of magnesium nitrate (3.0 g in terms of MgO) were added, and then 55.7 g (corresponding to 30 volume %) of $Y_2O_3$ (3 mol%) doped $ZrO_2$ powder (average particle size 0.8 μm) was added thereto little by little while stirring was continued. The mixture was thereafter successively stirred for 2 hours, cooled, and after addition of 1.2 g of 10% aqueous solution of hydrofluoric acid heated to 40° C. with stirring to form gel.

The gel was taken out and dried at 50° C. for one week. The dried gel was pulverized, heated to 700° C. at 20° C./hr and held at the temperature for 2 hours to carry out heat treatment.

The heat-treated powder was pulverized by a ball mill, molded with a CIP under a water pressure of 4000 kg/cm², and then sintered under atmospheric pressure at 1200° C. for 3 hours.

The resulting sintered body contained crystals of apatite and wollastonite besides the mixed zirconia.

The evaluation of dynamic properties of the sintered bodies revealed remarkable enhancement of the properties in the sintered body obtained by the present example. Namely, the bending strength and fracture toughness of the sintered body not containing the $ZrO_2$ powder (comparative example) were 2000 kg/cm² and 1.7 MPa·m½ respectively, but those of the sintered body obtained by the present example were 5100 kg/cm² and 4.0 MPa·m½ respectively.

EXAMPLE 3

114.0 g of tetraethyoxysilane (32.9 g in terms $SiO_2$), 24.2 g (12.5 g in terms of $P_2O_5$) of the mixture of monoethyl phosphate and diethyl phosphate (molar ratio: 50/50), and 100 g of 0.2 mol/l aqueous solution of hydrochloric acid were mixed and stirred at room temperature. After one hour, 119.5 g of 50% aqueous solution of calcium nitrate (20.4 g in terms of CaO) and 10.5 g of 50% aqueous solution of sodium nitrate (1.9 g in terms of $Na_2O$) were added, and then 75.9 g (corresponding to 30 volume %) of $Y_2O_3$ (3 mol %) doped $ZrO_2$ powder (average particle size: 0.8 μm) and 16.6 g (corresponding to 10 volume %) of α-$Al_2O_3$ powder (average particle size: 1.8 μm) were added little by little while stirring was continued. After continuing stirring for 2 hours, the mixture was heated to 80° C. with stirring to form gel.

After cooling to room temperature, the gel was taken out, dried at 50° C. for one week, and pulverized. The resulting gel powder was heated to 500° C. at 20° C./hr and held at the temperature for 5 hours to carry out heat-treatment.

The heat-treated powder was pulverized by a ball mill and then sintered in the same manner as in Example 1.

The resulting sintered body contained crystals of apatite and wollastonite besides zirconia and alumina.

The evaluation of dynamic properties of the sintered body revealed remarkable enhancement of the properties. Namely, the bending strength and fracture toughness of the sintered body not containing the $ZrO_2$ powder nor —$Al_2O_3$ powder were 1800 $kg/cm^2$ and 1.5 $MPa \cdot m^{\frac{1}{2}}$ respectively. However, those of the sintered body obtained by the present example were 4800 $kg/cm^2$ and 3.7 $MPa \cdot m^{\frac{1}{2}}$ respectively.

EXAMPLE 4

87.8 g of tetraethoxysilane (25.4 g in terms of $SiO_2$), 8.2 g (4.3 g in terms of $P_2O_5$) of the mixture of monoethyl phosphate and diethyl phosphate (molar ratio: 50/50), and 80 g of 0.2 mol/l aqueous solution of hydrochloric acid were mixed and stirred at room temperature. After one hour, 180 g of 50% aqueous solution of calcium nitrate (30.8 g in terms of CaO) was added thereto.

Separately, $Y_2O_3$ (3 mol %) doped $ZrO_2$ powder (average particle size: 0.3 μm) and α-$Al_2O_3$ powder (average particle size: 0.4 μm) were mixed to a volume ratio of 3:2, calcined at 1400° C. for 2 hours, and pulverized by a ball mill to the particle size of 3 μm or less to prepare mixed powder.

77.8 g of the mixed powder (corresponding to 40 volume %) was added little by little to the above reaction solution with stirring. After stirring had been continued for 2 hours, the mixture was heated to 80° C. with stirring to form gel and then cooled to room temperature. The gel was taken out, dried at 50° C. for one week and then pulverized. The resulting gel powder was heated to 500° C. at 20° C./hr and held at the temperature for 5 hours to carry out heat-treatment.

The heat-treated powder was pulverized by a ball mill and then sintered in the same manner as in Example 1.

The resulting sintered body contained crystals of apatite and wollastonite besides zirconia and alumina.

The evaluation of dynamic properties of the sintered body revealed remarkable enhancement of the properties. Namely, the bending strength and fracture toughness of the sintered body not containing the $ZrO_2$ and α-$Al_2O_3$ were 1700 $kg/cm^2$ and 1.4 $MPa \cdot m^{\frac{1}{2}}$ respectively. However, those of the sintered body obtained by the present example were 5000 $kg/cm^2$ and 3.8 $MPa \cdot m^{\frac{1}{2}}$ respectively.

EXAMPLE 5

114.6 g of tetraethoxysilane (33.1 g in terms of $SiO_2$), 13.2 g (6.8 g in terms of $P_2O_5$) of the mixture of monoethyl phosphate and diethyl phosphate (molar ratio: 50/50), and 100 g of 0.2 mol/l aqueous solution of hydrochloric acid were mixed and stirred at room temperature. After one hour, 131.6 g of 50% aqueous solution of calcium nitrate (22.5 g in terms of CaO) was added, and then 24.6 g (corresponding to 25 volume %) of β-SiC whisker (diameter: 0.1 to 1.0 μm, length: 20 to 200 μm) was added thereto little by little with stirring. Thereafter, stirring was continued for 2 hours, temperature was elevated to 80° C. and stirring continued. About 20 minutes later the reaction liquid thickened and gelled. After cooling to room temperature the gel was taken out, dried at 50° C. for one week and then pulverized. The resulting gel powder was heated to 500° C. at 20° C./hr and held at the temperature for 5 hours to carry out heat treatment.

The heat-treated powder was pulverized by a ball mill and then sintered by a hot press in an argon atmosphere under the pressure of 400 $kg/cm^2$ at 1200° C. for 2 hours.

The resulting sintered body contained crystals of apatite and wollustonite besides the mixed silicon carbide.

The evaluation of dynamic properties of the sintered body revealed remarkable enhancement of the properties. Namely, the bending strength and fracture toughness of the sintered body not containing β-SiC whisker were 2100 $kg/cm^2$ and 1.7 $MPa \cdot m^{\frac{1}{2}}$ respectively. However, those of the sintered body obtained by the present example were 4900 $kg/cm^2$ and 4.7 $MPa \cdot m^{\frac{1}{2}}$ respectively.

EXAMPLE 6

97.1 g of tetraethoxysilane (28.1 g in terms of $SiO_2$), 24.0 g of 85% orthophosphoric acid (14.8 g in terms of $P_2O_5$) and 200 g of water were mixed and stirred at room temperature. After one hour, 140.8 g of 50% aqueous solution of calcium nitrate (24.1 g in terms of CaO) were added thereto, and then 61.7 g (corresponding to 30 volume %) of $Y_2O_3$ (6 mol %) doped $ZrO_2$ length: 2000 μm) were added little by little with stirring. After stirring had been continued for 2 hours, the mixture was cooled and 1.6 g of 10% aqueous solution of hydrofluoric acid was added. The mixture was warmed to 40° C. with stirring to form gel. After drying at 50° C. for one week, the gel was heated to 700° C. at 20° C./hr and held at the temperature for 3 hours to carry out heat treatment.

The heat-treated powder was pulverized, molded by a CIP under a water pressure of 4000 $kg/cm^2$, and then sintered atmospheric pressure at 1200° C. for 3 hours.

The obtained sintered body contained crystals of apatite besides the mixed zirconia.

The evaluation of dynamic properties of the sintered body revealed remarkable enhancement of the properties. Namely, the bending strength and fracture toughness of the sintered body not containing the $ZrO_2$ short fiber were 1700 $kg/cm^2$ and 1.5 $MPa \cdot m^{\frac{1}{2}}$ respectively. However, those of the sintered body obtained by the present example were 4400 $kg/cm^2$ and 4.5 $MPa \cdot m^{\frac{1}{2}}$ respectively.

EXAMPLE 7

131.2 g of tetraethoxysilane (37.9 g in terms of $SiO_2$), 14.8 g (7.7 g in terms of $P_2O_5$) of the mixture of monoethyl phosphate and diethyl phosphate (molar ratio: 50/50), and 120 g of 0.15 mol/l aqueous solution of hydrochloric acid were mixed and stirred at room temperature. One hour later, 103.4 g of 50% aqueous solution of calcium nitrate (17.7 g in terms of CaO), 77.3 g of 30% aqueous solution of magnesium nitrate (6.3 g in terms of MgO) and 13.7 g of 50% aqueous solution of sodium nitrate (2.5 g in terms of $Na_2O$) were added, and then 36.0 g (corresponding to 30 volume %) of the same β-SiC whisker as used in Example 5 was added little by little with stirring. After stirring had been continued for 2 hours, the mixture was heated to 80° C. to form gel. The gel was dried and heat-treated in the same manner as in Example 5.

The heat-treated powder was pulverized by a ball mill and sintered in the same manner as in Example 5 except for using the temperature of 1100° C.

The obtained sintered body contained crystals of apatite and wollastonite besides the mixed silicon carbide.

The evaluation of dynamic properties of the sintered body revealed remarkable enhancement of the properties. Namely, the bending strength and fracture toughness of the sintered body not containing β-SiC whisker were 2300 kg/cm$^2$ and 1.8 MPa·m$^{\frac{1}{2}}$ respectively. However, those of the sintered body obtained by the present example were 5200 kg/cm$^2$ and 5.3 MPa·m$^{\frac{1}{2}}$ respectively.

EXAMPLE 8

In the composition ratio $SiO_2/CaO/P_2O_5=47/45/8$ (weight ratio), tetraethoxysilane, the mixture of monoethyl phosphate and diethyl phosphate (molar ratio: 50/50), and water in an amount of 12 times (molar ratio) the amount of tetraethoxysilane were mixed and stirred at room temperature for one hour, and then 50% aqueous solution of calcium nitrate was added.

The following additives No. 1, i.e. $Y_2O_3$ (2 mol %) doped $ZrO_2$ powder (average particle size: 0.3 μm) state and No. 2, i.e. β-SiC whisker (diameter: 0.1 to 1.0 μm, length: 20 to 200 μm) as reinforcing materials were added little by little to the thus prepared solution with stirring, in the respective amounts shown in the following stirred for one hour and heated to 80° C. to form gel. After cooling to room temperature, the gel was taken out and dried at 50° C. for one week. The dried gel was heated to 500° C. at 10° C./hr and held at the temperature for 10 hours to carry out heat treatment.

The heat-treated powder was pulverized by a ball mill, and sintered by a hot press in an argon atmosphere under the pressure of 400 kg/cm$^2$ at 1050° C. for 2 hour to obtain sintered body.

On the other hand, silicon dioxide, calcium carbonate and calcium hydrogen phosphate (dihydrate) were thoroughly mixed in powder state to the same composition ratio as above, placed in a platinum crucible, and heated at 1600° C. for one hour to melt the mixture. The melted mixture was poured into water for quenching, the quenched mixture was dried and pulverized by a ball mill to particle size of 44 μm (325 mesh) or less to obtain glass powder.

The following additives No. 3, i.e. the same additive as No. 1, and No. 4, i.e. the same additive as No. 2 were added as reinforcing materials to the above glass powder in the same amounts with No. 1 and No. 2 respectively (as shown in the table), and mixed using a ball mill. The mixtures were sintered by a hot press in the same manner as in Nos. 1 and 2 to obtain sintered bodies.

The thus obtained No. 1 to No. 4 sintered bodies each contained crystals of apatite and wollastonite besides the respective additives.

The bending strength of these sintered bodies was measured, and the Weibull modulus was determined for evaluation of scattering of the strength (number of specimen: 40). The results are shown in the following table.

|  | No. | Additive (volume %) | | Average flexural strength (kg/cm$^2$) | Weibull coefficient |
|---|---|---|---|---|---|
|  |  | $ZrO_2$ powder | SiC whisker |  |  |
| Present invention | 1 | 45 | — | 5100 | 19.6 |
|  | 2 | — | 30 | 4800 | 21.3 |
| Comparative example | 3 | 45 | — | 4500 | 10.7 |
|  | 4 | — | 30 | 4400 | 13.8 |

It is seen from the above result that the sintered bodies of the invention (Nos. 1 and 2) prepared using the sol-gel method had enhanced strength as compared with the sintered bodies (Nos. 3 and 4) prepared by mixing the reinforcing material with the glass powder obtained by the melting method and sintering the mixture. Further, it is also seen from the above result that according to the invention there can be obtained composite sintered bodies which have larger Weibull coefficient, i.e. much reduced scattering of the strength and thus are more homogeneous, which is a more remarkable effect than the above effect.

EXAMPLE 9

116.7 g of tetraethoxysilane (33.7 g in terms of $SiO_2$), g (5.0 g in terms of $P_2O_5$) of the mixture of monoethyl phosphate and diethyl phosphate (molar ratio: 50/50), and 100 g of 0.2 mol/l aqueous solution of hydrochloric acid were mixed and stirred at 40° C.. One hour later, 132.6 g of 50% aqueous solution of calcium nitrate (22.7 g in terms of CaO) was added, and then 23.7 g (corresponding to 20 volume %) of β-SiC whisker (diameter: 0.1 to 1.0 m, length: 20 to 200 μm) and 45.0 g (corresponding to 20 volume %) of $Y_2O_3$ (3 mol %) doped $ZrO_2$ powder (average particle size: 0.8 μm) were each added little by little with stirring. After stirring had been continued for 2 hours, the mixture was heated to 80° C. and successively stirred. About 20 minutes later the reaction mixture thickened and gelled. After cooling to room temperature, the gel was taken out and dried at 50° C. for one week. After successive pulverization, the dried gel power was heated to 500° C. at 20° C./hr and held at the temperature for 5 hours to carry out heat treatment.

The heat-treated powder was pulverized using a ball mill, and sintered by a hot press in an argon atmosphere under a pressure of 400 kg/cm$^2$ at 1200° C. for 2 hours.

The resulting sintered body contained crystals of apatite and wollastonite besides the mixed silicon carbide and zirconia.

The evaluation of dynamic properties of this sintered body revealed remarkable enhancement of the properties. Namely, the bending strength and fracture toughness of the sintered body not containing β-SiC whisker nor the ZrO$_2$ powder were 1700 kg/cm$^2$ and 1.4 MPa·m$^{\frac{1}{2}}$ respectively. However, those of the sintered body obtained by the present example were 4200 kg/cm$^2$ and 7.8 MPa·m$^{\frac{1}{2}}$ respectively.

EXAMPLE 10

51.9 g of tetramethoxysilane (23.3 g in terms of SiO), 14.3 g of 85% orthophosphoric acid (8.8 g in terms of P$_2$) and 105 g of water were mixed and stirred at room temperature. One hour later, 180.5 g of 50% aqueous solution of calcium nitrate (30.9 g in terms of CaO) and 65.0 g of 30% aqueous solution of magnesium nitrate (5.3 g in terms of MgO) were added. Then with continuation of stirring, 36.1 g (corresponding to 15 volume %) of Y$_2$O$_3$ (6 mol %) doped ZrO$_2$ short fibers (average diameter: 5 μm, average fiber length: 2000 μm) and 62.8 g (corresponding to 25 volume %) of Y$_2$O$_3$ (6 mol %) doped ZrO$_2$ powder (average particle size: 1 μm) were each added little by little. After continuation of stirring for 2 hours, the mixture was heated to 70° C. to form gel. After cooling to room temperature, the gel was taken out, dried at 50° C. for one week and then pulverized. The resulting powder was heated to 800° C. at 20° C./hr and held at the temperature for 2 hours to carry out heat treatment.

The heat-treated powder was pulverized by a ball mill, molded by a CIP under a water pressure of 4000 kg/cm$^2$, and sintered under an argon pressure of 9.8 kg/cm$^2$ at 1100° C. for 2 hours.

The resulting sintered body contained crystals of apatite and wollastonite besides the mixed zirconia.

The evaluation of dynamic properties of this sintered body revealed remarkable enhancement of the properties. Namely, the bending strength and fracture toughness of the sintered body not containing the ZrO$_2$ short fibers and the ZrO$_2$ powder as set out above were 2100 kg/cm$^2$ and 1.8 MPa·m$^{\frac{1}{2}}$ respectively. However, those of the sintered body obtained by the present example were 4500 kg/cm$^2$ and 7.3 MPa·m$^{\frac{1}{2}}$ respectively.

EXAMPLE 11

110.9 g of tetraethoxysilane (32.0 g in terms of SiO$_2$), 18.4 g (9.5 g in terms of P$_2$O$_5$) of the mixture of monoethyl phosphate and diethyl phosphate (molar ratio: 50/50) and 150 g of water were mixed and stirred at room temperature. One hour later, 131.3 g of 50% aqueous solution of calcium nitrate (22.4 g in terms of CaO) was added, and with continuation of stirring 15.9 g (corresponding to 15 volume %) of β-SiC whisker (diameter: 0.1 to 1.0 μm, length: 50 to 200 μm) was added little by little.

Separately, Y$_2$O$_3$ (3 mol %) doped ZrO$_2$ powder (average particle size: 0.3 μm) and α-Al$_2$O$_3$ powder (average particle size 0.4 μm) were mixed to a volume ratio of 7:3, calcined at 1400° C. for 2 hours, and pulverized by a ball mill to a particle size of 3 μm or less.

Then, 27.1 g (corresponding to 15 volume %) of the thus prepared mixed powder of the ZrO$_2$ and α-Al$_2$O$_3$ was added little by little to the above reaction solution with stirring.

After continuation of stirring for 2 hours, the mixture was cooled, and after addition of 1.5 g of 10% aqueous solution of hydrofluoric acid the mixture was warmed to 40° C. with stirring to form gel. The resulting gel was dried, heat-treated and sintered by a hot press, in the same manner as in Example 9.

The resulting sintered body contained crystals of apatite and wollastonite besides the mixed silicon carbide, zirconia and alumina.

The evaluation of dynamic properties of this sintered body revealed remarkable enhancement of the properties. Namely, the bending strength and fracture toughness of the sintered body not containing β-SiC whisker nor mixed powder of the ZrO$_2$ with α-Al$_2$O$_3$ were 2300 kg/cm$^2$ and 1.9 MPa·m$^{\frac{1}{2}}$ respectively. However, those of the sintered body obtained by the present example were 5100 kg/cm$^2$ and 8.5 MPa·m$^{\frac{1}{2}}$ respectively.

What is claimed is:

1. A process for preparing a glass or glass-ceramic composite sintered body which comprises reacting
   (A) at least one silicic acid ester represented by the general formula (I)

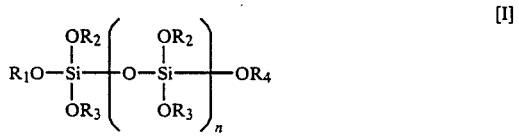

wherein R$_1$ to R$_4$ are each hydrogen or a group represented by C$_x$H$_{2x+1}$(OC$_2$H$_4$)$_y$— where x is 1 to 5, and y is 0 to 10, provided that R$_1$ to R$_4$ are not all hydrogen at the same time and n is 0 to 20;
   (B) at least one phosphorus compound represented by the general formula (II), (III) or (IV):

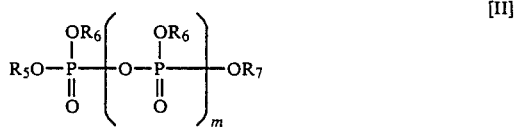

wherein R$_5$ to R$_9$ are each hydrogen, an alkyl group having 1 to 5 carbon atoms, a phenyl group or an aralkyl group having 7 to 10 carbon atoms, and m is 0 to 10 and;
   (C) at least one compound selected from the group consisting of water-soluble calcium salts; with water in an amount necessary for hydrolyzing the components (A)–(C) in the presence of the following component (D-1) and/or the following component (D-2) to form a gel, and drying, molding and then sintering the gel;
   (D-1): at least one kind of ceramics fine particles having a composition different from a sintered body obtained from components (A) to (C) or having a crystal different from crystals formed in the sintered body,
   (D-2): ceramic short fibers and/or whiskers.

2. The process of claim 1 wherein the ceramics fine particles are selected from the group consisting of Al$_2$O$_3$, ZrO$_2$, SiC, Si$_3$N$_4$, BN and sialon.

3. The process of claim 1 wherein the ceramics fine particles are polycrystals or single crystals having a melting point above the sintering temperature.

4. The process of claim 1 wherein the particle size of the ceramic fine particles is 10 μm or less.

5. The process of claim 1 wherein the ceramics short fibers and/or the whiskers are those of an oxide, a carbide, a nitride, an oxynitride or a boride.

6. The process of claim 1 wherein the ceramics short fibers and/or the whiskers are those of $Al_2O_3$, $ZrO_2$, SiC, $SiN_4$, BN or sialon.

7. The process of claim 1 wherein the ceramics short fibers and/or the whiskers have an aspect ratio of 5 or more.

8. The process of claim 1 wherein component (D-1) is used in an amount of 5 to 60 volume % in the composite sintered body.

9. The process of claim 1 wherein component (D-2) is used in an amount of 5 to 50 volume % in the composite sintered body.

10. The process of claim 1 wherein components (D-1) and (D-2) are used together in a total amount of 10 to 60 volume % in the composite sintered body.

11. The process of claim 1 wherein the gel after the drying and before the molding is either powdered and then heat-treated, or heat-treated and then powdered.

12. The process of claim 11 wherein the heat treatment is carried out at a temperature lower than the sintering temperature and equal to or higher than 200° C.

13. The process of claim 1 wherein the sintering is carried out at 800° to 1300° C.

* * * * *